(12) United States Patent
Daw et al.

(10) Patent No.: US 8,795,195 B2
(45) Date of Patent: Aug. 5, 2014

(54) GRAPHICAL USER INTERFACE FOR TISSUE BIOPSY SYSTEM

(75) Inventors: Derek Daw, Costa Mesa, CA (US); Frank R. Louw, Carlsbad, CA (US); Paul Lubock, Laguna Niguel, CA (US); Richard L. Quick, Mission Viejo, CA (US); Martin V. Shabaz, Lake Forest, CA (US)

(73) Assignee: SenoRx, Inc., Tempe, AZ (US)

( * ) Notice: Subject to any disclaimer, the term of this patent is extended or adjusted under 35 U.S.C. 154(b) by 2227 days.

(21) Appl. No.: 11/284,641

(22) Filed: Nov. 22, 2005

(65) Prior Publication Data

US 2006/0149162 A1    Jul. 6, 2006

Related U.S. Application Data

(60) Provisional application No. 60/631,338, filed on Nov. 29, 2004.

(51) Int. Cl.
    *A61B 10/02*      (2006.01)
    *G06F 3/16*      (2006.01)

(52) U.S. Cl.
    USPC ............ 600/564; 600/562; 382/128; 715/700

(58) Field of Classification Search
    USPC .......... 600/562, 564; 382/128, 130, 131, 132; 715/700
    See application file for complete search history.

(56) References Cited

U.S. PATENT DOCUMENTS

| | | | |
|---|---|---|---|
| 3,844,272 A | 10/1974 | Banko | |
| 4,517,976 A | 5/1985 | Murakoshi et al. | |
| 4,658,819 A | 4/1987 | Harris et al. | |
| 4,739,759 A | 4/1988 | Rexroth et al. | |
| 4,769,850 A * | 9/1988 | Itoh et al. | 382/132 |
| 4,878,493 A | 11/1989 | Pasternak et al. | |
| 5,159,929 A | 11/1992 | Morris et al. | |
| 5,400,267 A | 3/1995 | Denen et al. | |
| 5,415,169 A | 5/1995 | Siczek et al. | |
| 5,549,112 A * | 8/1996 | Cockburn et al. | 600/461 |

(Continued)

FOREIGN PATENT DOCUMENTS

| | | |
|---|---|---|
| DE | 37 03 218 | 8/1988 |
| EP | 0 225 973 | 6/1987 |

(Continued)

OTHER PUBLICATIONS

*Force FX™ Electrosurgical Generator Instant Response to Tissue Density*, Instant Response Technology, http://www.valleylab.com/PRODUCTS/ fx.htm, electrosurgical Generators pp. 1-4.

(Continued)

*Primary Examiner* — Sean Dougherty

(57) ABSTRACT

A graphical user interface is disclosed for a tissue biopsy system having a tissue cutting member adapted for cutting one or more tissue specimens from tissue at a target site within a patient. The graphical user interface includes a first GUI area representing a first region of the target site from which the tissue cutting member has separated one or more tissue specimens. The graphical user interface further includes a second GUI area, visually distinguishable from the first GUI area, representing a second region from which the tissue cutting member may separate one or more additional tissue specimens from tissue at the target site.

29 Claims, 15 Drawing Sheets

(56) References Cited

U.S. PATENT DOCUMENTS

| | | | |
|---|---|---|---|
| 5,609,152 A * | 3/1997 | Pellegrino et al. | 600/429 |
| 5,617,857 A | 4/1997 | Chader et al. | |
| 5,640,956 A | 6/1997 | Getzinger et al. | |
| 5,643,255 A * | 7/1997 | Organ | 606/41 |
| 5,728,124 A * | 3/1998 | Cockburn et al. | 604/22 |
| 5,749,869 A | 5/1998 | Lindenmeier et al. | |
| 5,769,086 A | 6/1998 | Ritchart et al. | |
| 5,772,659 A | 6/1998 | Becker et al. | |
| 5,807,304 A * | 9/1998 | Cockburn | 604/19 |
| 5,829,439 A * | 11/1998 | Yokosawa et al. | 600/461 |
| 5,848,177 A * | 12/1998 | Bauer et al. | 382/128 |
| 5,849,009 A | 12/1998 | Bernaz | |
| 5,976,128 A | 11/1999 | Schilling et al. | |
| 5,997,535 A | 12/1999 | Betsill et al. | |
| 6,022,325 A * | 2/2000 | Siczek et al. | 600/568 |
| 6,022,347 A | 2/2000 | Lindenmeier et al. | |
| 6,036,681 A | 3/2000 | Hooven | |
| 6,066,096 A * | 5/2000 | Smith et al. | 600/439 |
| 6,066,134 A | 5/2000 | Eggers et al. | |
| 6,117,126 A | 9/2000 | Appelbaum et al. | |
| 6,162,216 A | 12/2000 | Guziak et al. | |
| 6,216,029 B1 * | 4/2001 | Paltieli | 600/427 |
| 6,217,510 B1 * | 4/2001 | Ozawa et al. | 600/129 |
| 6,238,342 B1 * | 5/2001 | Feleppa et al. | 600/437 |
| 6,246,782 B1 * | 6/2001 | Shapiro et al. | 382/128 |
| 6,351,660 B1 * | 2/2002 | Burke et al. | 600/425 |
| 6,370,411 B1 | 4/2002 | Osadchy et al. | |
| 6,391,024 B1 | 5/2002 | Sun et al. | |
| 6,432,065 B1 | 8/2002 | Burdorff et al. | |
| 6,436,054 B1 * | 8/2002 | Viola et al. | 600/562 |
| 6,458,121 B1 | 10/2002 | Rosenstock et al. | |
| 6,632,183 B2 | 10/2003 | Bowman et al. | |
| 6,981,941 B2 | 1/2006 | Whitman et al. | |
| 7,092,557 B2 * | 8/2006 | Eisfeld et al. | 382/128 |
| 7,184,582 B2 * | 2/2007 | Giger et al. | 382/128 |
| 7,465,090 B2 * | 12/2008 | Haras | 378/206 |
| 7,465,279 B2 * | 12/2008 | Beckman et al. | 600/566 |
| 7,496,398 B2 * | 2/2009 | Nields et al. | 600/427 |
| 7,542,791 B2 * | 6/2009 | Mire et al. | 600/407 |
| 7,598,088 B2 * | 10/2009 | Balas | 436/172 |
| 7,660,623 B2 * | 2/2010 | Hunter et al. | 600/424 |
| 7,693,567 B2 * | 4/2010 | Tsonton et al. | 600/411 |
| 8,005,529 B2 * | 8/2011 | Ramzipoor et al. | 600/407 |
| 2002/0077565 A1 | 6/2002 | Burdorff et al. | |
| 2002/0198519 A1 | 12/2002 | Qin et al. | |
| 2003/0050553 A1 * | 3/2003 | Samoszuk et al. | 600/410 |
| 2003/0114862 A1 * | 6/2003 | Chu et al. | 606/130 |
| 2003/0130711 A1 | 7/2003 | Pearson et al. | |
| 2003/0139700 A1 * | 7/2003 | Elliott et al. | 604/62 |
| 2003/0144605 A1 | 7/2003 | Burbank et al. | |
| 2003/0181898 A1 | 9/2003 | Bowers | |
| 2003/0233054 A1 * | 12/2003 | Stephens et al. | 600/566 |
| 2004/0030334 A1 | 2/2004 | Quick et al. | |
| 2004/0061498 A1 * | 4/2004 | Ochi et al. | 324/318 |
| 2004/0077938 A1 * | 4/2004 | Mark et al. | 600/411 |
| 2004/0082945 A1 | 4/2004 | Clague et al. | |
| 2004/0114146 A1 * | 6/2004 | Willis | 356/446 |
| 2004/0153005 A1 * | 8/2004 | Krueger | 600/571 |
| 2004/0171924 A1 * | 9/2004 | Mire et al. | 600/407 |
| 2004/0171986 A1 * | 9/2004 | Tremaglio et al. | 604/116 |
| 2004/0172017 A1 | 9/2004 | Marion et al. | |
| 2004/0181219 A1 | 9/2004 | Goble et al. | |
| 2004/0184644 A1 * | 9/2004 | Leichter et al. | 382/128 |
| 2004/0202357 A1 * | 10/2004 | Perz et al. | 382/128 |
| 2004/0234113 A1 * | 11/2004 | Miga | 382/128 |
| 2004/0252870 A1 * | 12/2004 | Reeves et al. | 382/128 |
| 2004/0267121 A1 * | 12/2004 | Sarvazyan et al. | 600/439 |
| 2005/0004579 A1 * | 1/2005 | Schneider et al. | 606/108 |
| 2005/0058326 A1 * | 3/2005 | Barth et al. | 382/128 |
| 2005/0119646 A1 | 6/2005 | Scholl et al. | |
| 2005/0159676 A1 * | 7/2005 | Taylor et al. | 600/567 |
| 2005/0228311 A1 * | 10/2005 | Beckman et al. | 600/567 |
| 2006/0132790 A1 * | 6/2006 | Gutin | 356/479 |
| 2006/0141633 A1 * | 6/2006 | Balas | 436/164 |
| 2008/0187095 A1 * | 8/2008 | Boone et al. | 378/37 |
| 2009/0131821 A1 * | 5/2009 | Speeg et al. | 600/566 |
| 2010/0215226 A1 * | 8/2010 | Kaufman et al. | 382/128 |

FOREIGN PATENT DOCUMENTS

| | | | |
|---|---|---|---|
| EP | 1 051 948 | 11/2000 | |
| EP | 1 053 720 | 11/2000 | |
| EP | 1 082 945 | 3/2001 | |
| EP | 1 157 667 | 11/2001 | |
| EP | 1306054 A2 * | 5/2003 | A61B 8/08 |
| EP | 1 519 472 | 3/2005 | |
| EP | 1 527 743 | 5/2005 | |
| GB | 2 146 534 | 4/1985 | |
| JP | 2002 320325 | 10/2002 | |
| WO | WO 93/15655 | 8/1993 | |
| WO | WO 96/39088 | 12/1996 | |
| WO | WO 98/07378 | 2/1998 | |
| WO | WO 98/14129 | 4/1998 | |
| WO | WO 02/24082 | 3/2002 | |
| WO | 03077778 A1 | 9/2003 | |
| WO | 2004019799 A2 | 3/2004 | |
| WO | WO 2004/110294 | 12/2004 | |
| WO | WO 2005/060849 | 7/2005 | |

OTHER PUBLICATIONS

*New! Force EZ™ Electrosurgical Generator Instant Response to tissue Density*, Technology, http://www.valleylab.com/PRODUCTS/fx.htm, Electrosurgical Generators pp. 1-4.

*AmplifierModule 1-30MHz 150Watts*, LCF Enterprises RF Power Amplifiers, www.lcfamps.com, pp. 1-2.

International Search Report for PCT/US2005/042966, mailed Apr. 5, 2006.

Written Opinion of the International Searching Authority for PCT/US2005/042966, mailed Apr. 5, 2006.

\* cited by examiner

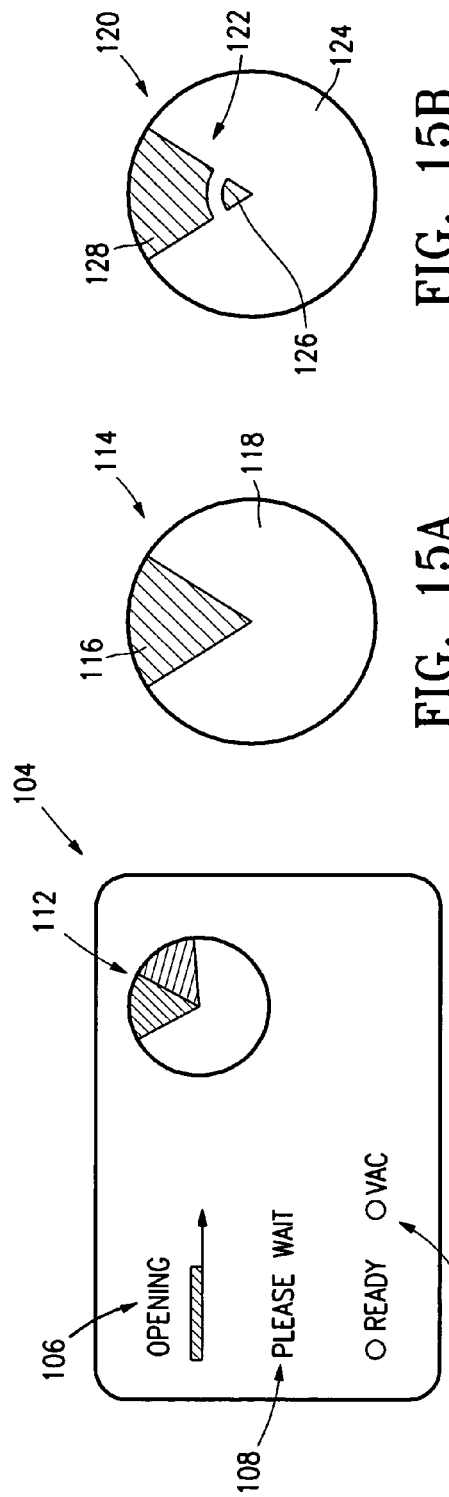
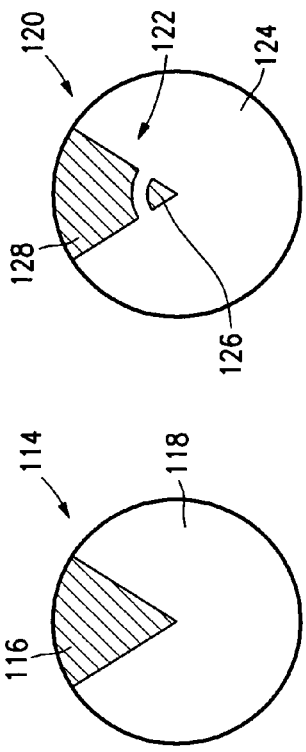
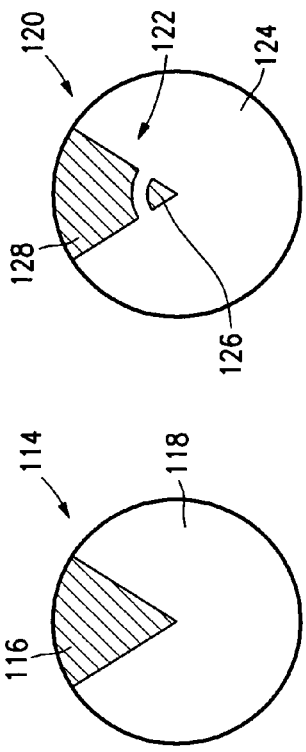
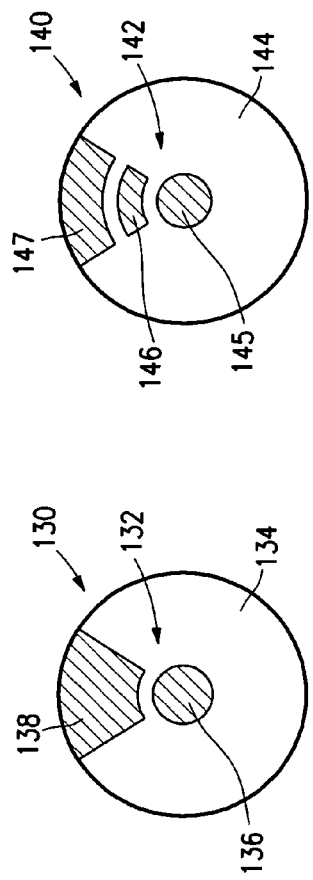
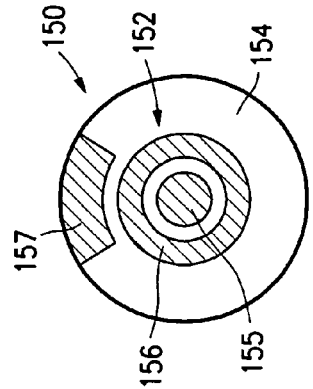
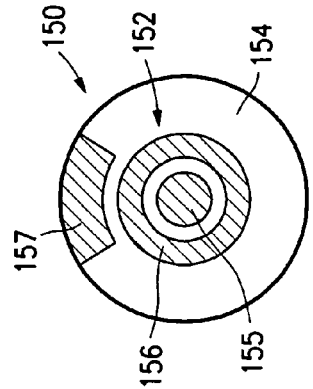

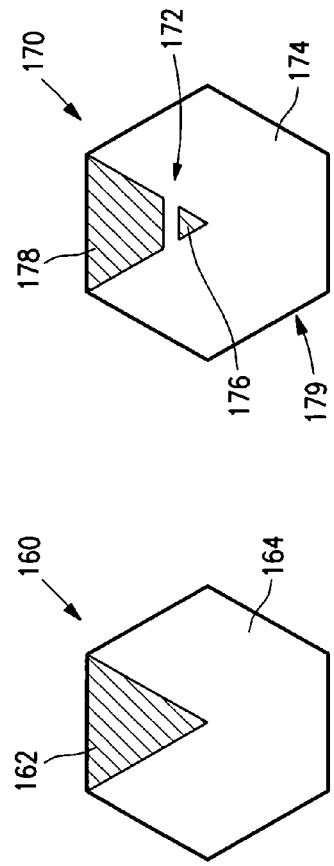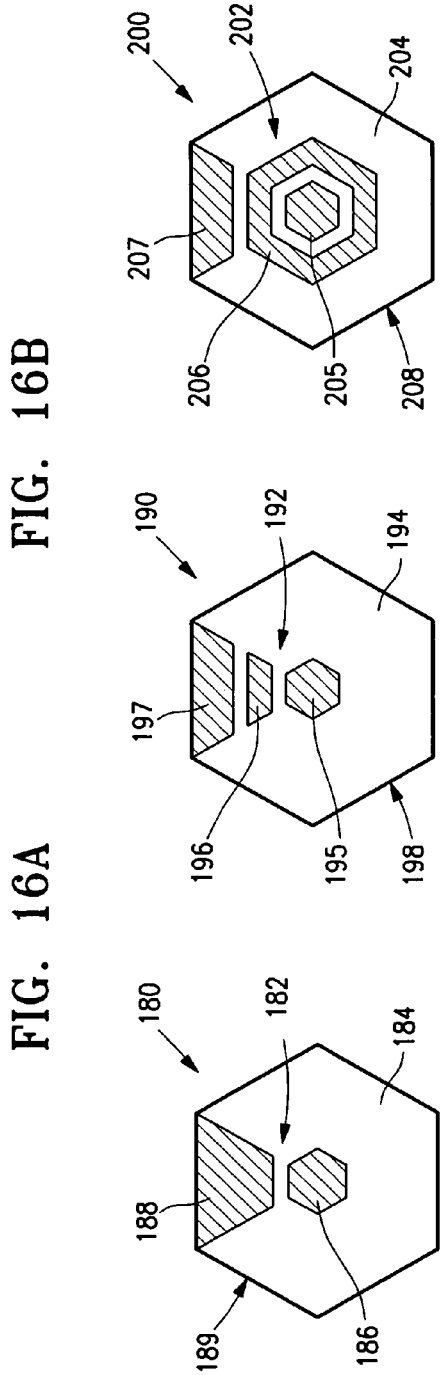
FIG. 16A
FIG. 16B
FIG. 16C
FIG. 16D
FIG. 16E

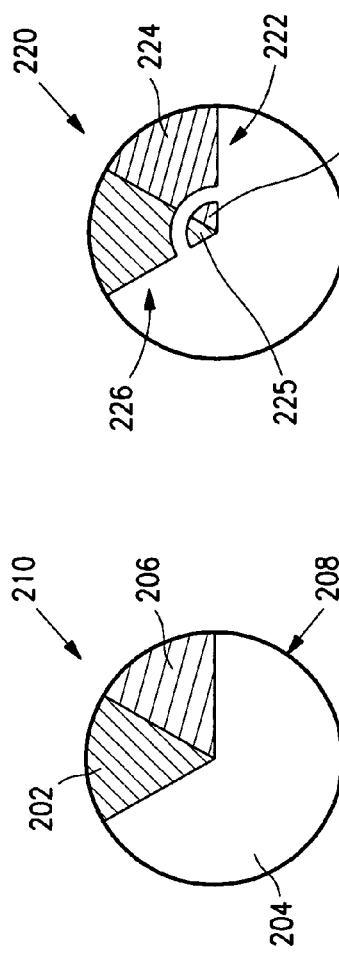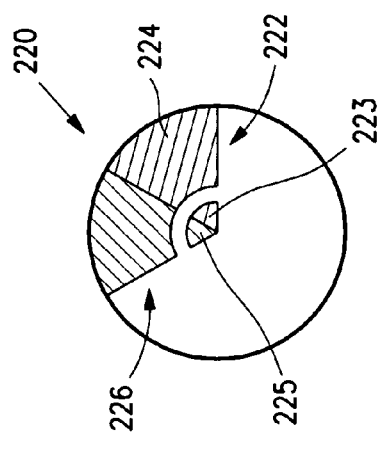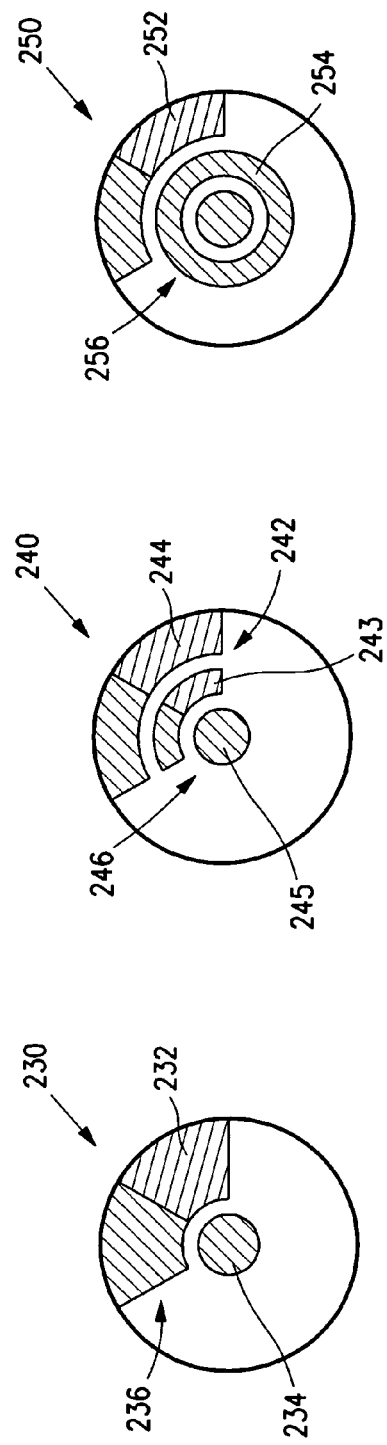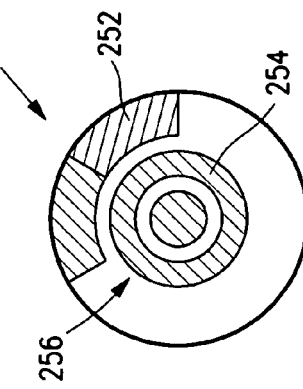

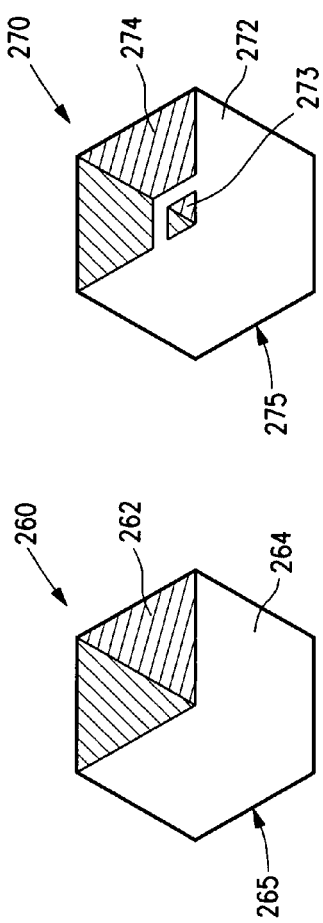
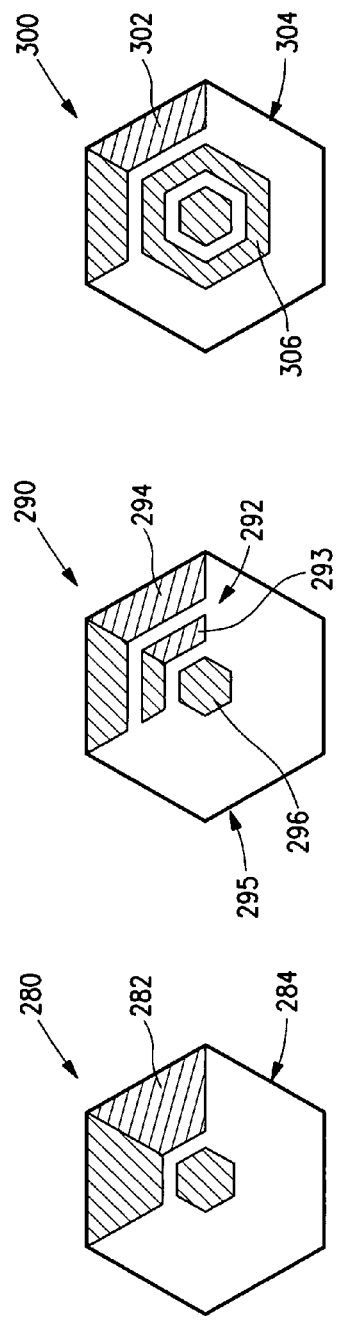
FIG. 18A
FIG. 18B
FIG. 18C
FIG. 18D
FIG. 18E

US 8,795,195 B2

GRAPHICAL USER INTERFACE FOR TISSUE BIOPSY SYSTEM

RELATED APPLICATIONS

This application is based on Provisional Application Ser. No. 60/631,338, filed on Nov. 29, 2004, and claims priority therefrom. The provisional application is incorporated by reference herein in its entirety.

FIELD OF THE INVENTION

The present invention relates generally to tissue removing devices such as biopsy devices. More specifically, it is directed to a graphical user interface (GUI) used in conjunction with the tissue removing devices.

BACKGROUND OF THE INVENTION

In diagnosing and treating certain medical conditions, such as potentially cancerous tumors, it is usually desirable to perform a biopsy, in which a specimen of the suspicious tissue is removed for pathological examination and analysis. In many instances, the suspicious tissue is located in a subcutaneous site, such as inside a human breast. To minimize surgical intrusion into the patient's body, it is desirable to be able to insert a small instrument into the patient's body to access the targeted site and to extract the biopsy specimen therefrom.

Electrosurgical techniques have been used in a variety of biopsy procedures. In electrosurgery, high frequency electrical energy is typically applied to patient tissue through an active electrode, the electrical circuit being completed by a return electrode in contact with the patent's tissue. Electrical energy flowing through the tissue from the active electrode is effective to ablate tissue near the active electrode, forming an opening in the tissue and so allowing insertion of the instrument into a patient's body. A return electrode may be placed on the exterior of the patient's body or may be incorporated into the device itself. The return electrode is typically attached to the patient at a point remote from where the primary or active electrode contacts the tissue.

Conventionally, when an electrosurgical biopsy instrument inserts into a patient's body, it's cutting end cannot be readily seen from outside. This makes it difficult for a surgeon to find out where the electrosurgical biopsy instrument is, in a biopsy operation. Thus, it is desirable to have a display device visually showing the location of the electrosurgical biopsy instrument with respect to the patient's body in biopsy operation.

SUMMARY OF THE INVENTION

The invention is directed to a graphical user interface for a tissue biopsy system having a tissue cutting member adapted for cutting one or more tissue specimens from tissue at a target site within a patient.

In one embodiment, the graphical user interface includes at least a first GUI area and a second GUI area. The first GUI area represents a first region of the target site from which the tissue cutting member has separated one or more tissue specimens. The second GUI area, visually distinguishable from the first GUI area, represents a second region from which the tissue cutting member may separate one or more additional tissue specimens from tissue at the target site.

BRIEF DESCRIPTION OF THE DRAWINGS

FIG. 14 illustrates a screen providing information with respect to an operation of the tissue biopsy system.

FIGS. 15A through 15E illustrate a number of alternative circular graphical user interfaces, each having a first GUI area and second GUI area representing various parts of a target site within a patient from which one or more tissue specimens haven been or may be separated from tissue.

FIGS. 16A through 16E illustrate a number of alternative polygonal graphical user interfaces, each having a first GUI area and second GUI area representing various parts of a target site within a patient from which one or more tissue specimens haven been or may be separated from tissue.

FIGS. 17A through 17E illustrate a number of alternative circular graphical user interfaces, each having a first, second and third GUI area representing various parts of a target site within a patient from which one or more tissue specimens haven been or may be separated or in which the tissue cutting element is deployed.

FIGS. 18A through 18E illustrate a number of alternative polygonal graphical user interfaces, each having a first, second and third GUI area representing various parts of a target site within a patient from which one or more tissue specimens haven been or may be separated, or in which the tissue cutting element is deployed.

DETAILED DESCRIPTION OF EMBODIMENTS OF THE INVENTION

Figure 1:
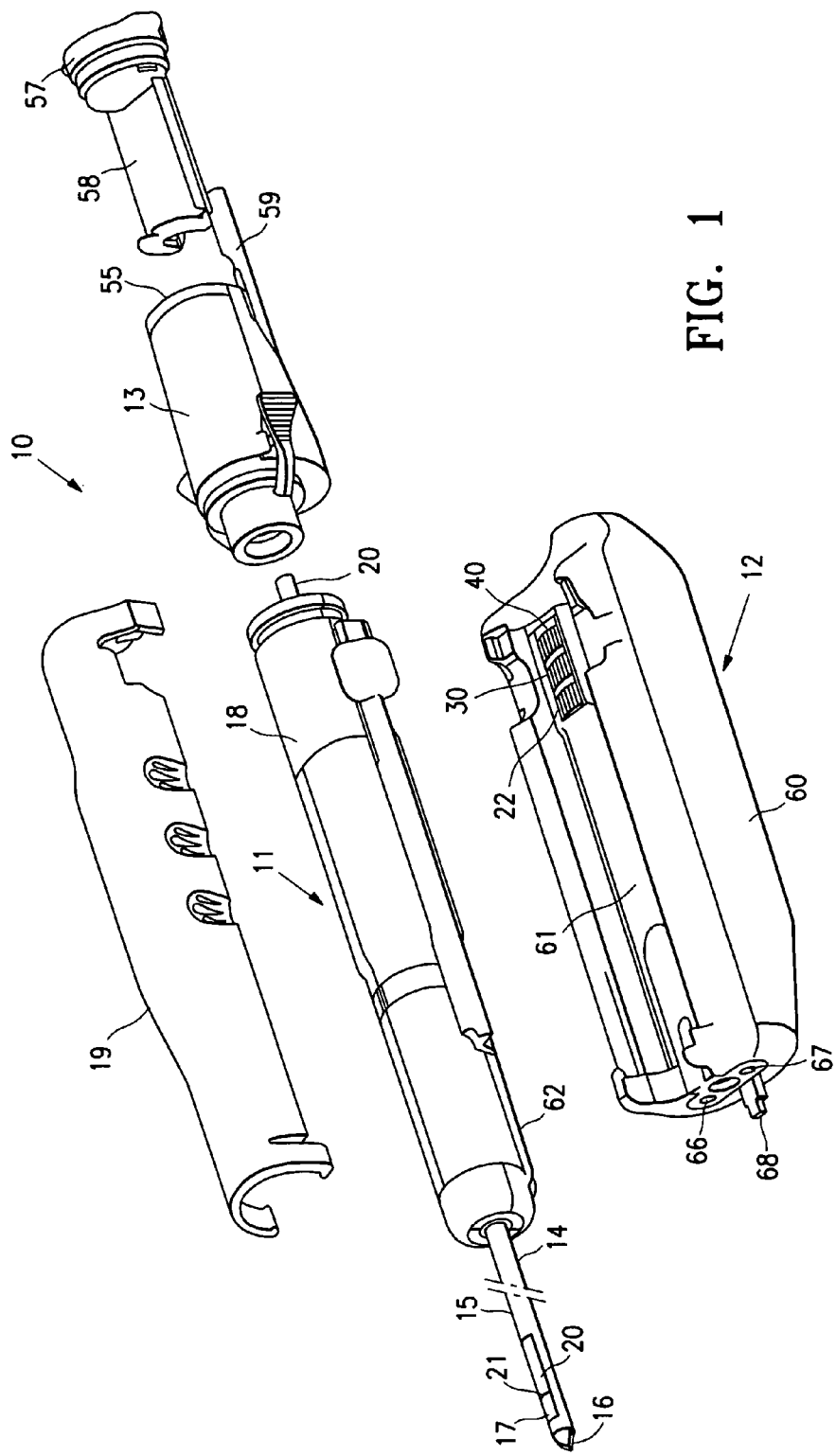
FIG. 1 is an exploded view of the elongated tissue biopsy system embodying features of the invention.
Figure 2:
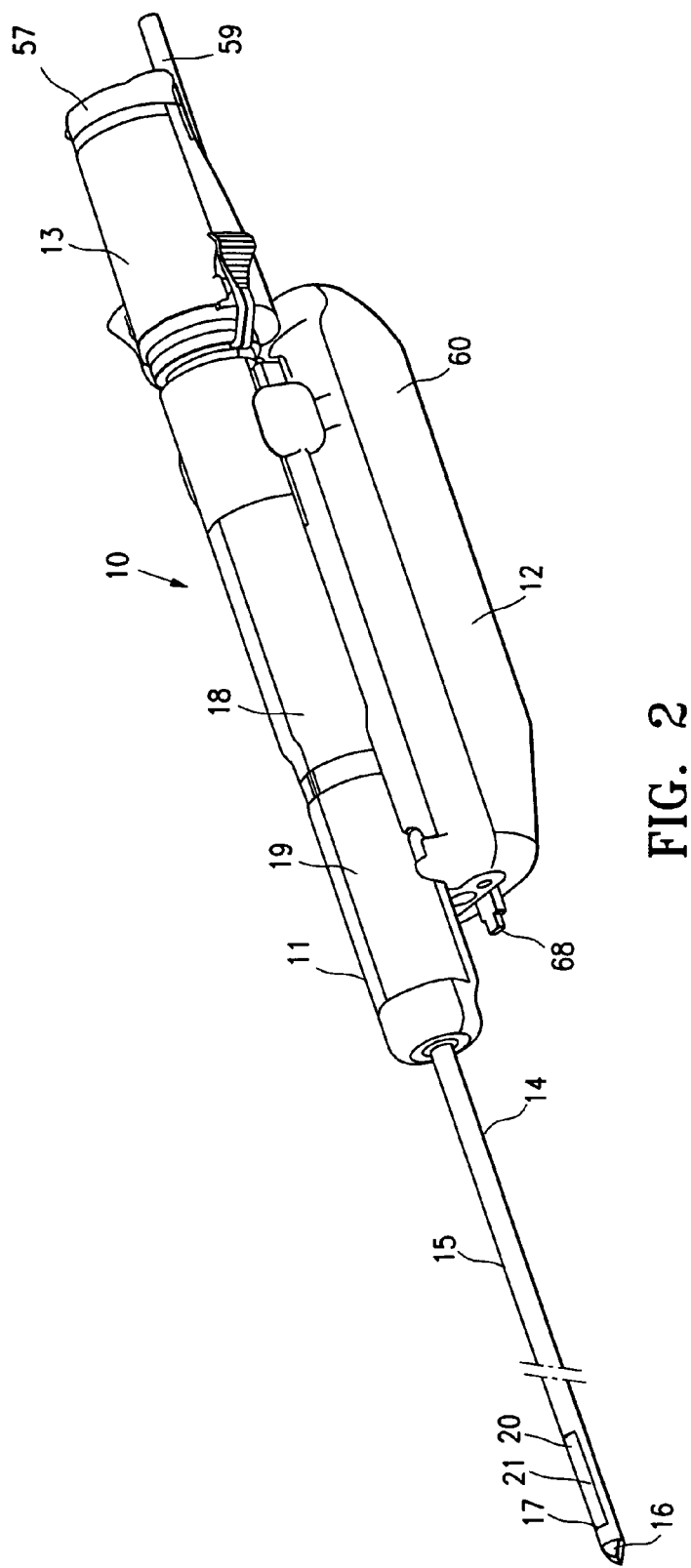
FIG. 2 is a perspective view of the embodiment shown in FIG. 1 in an assembled condition without a housing cover for the probe component.
Figure 3:
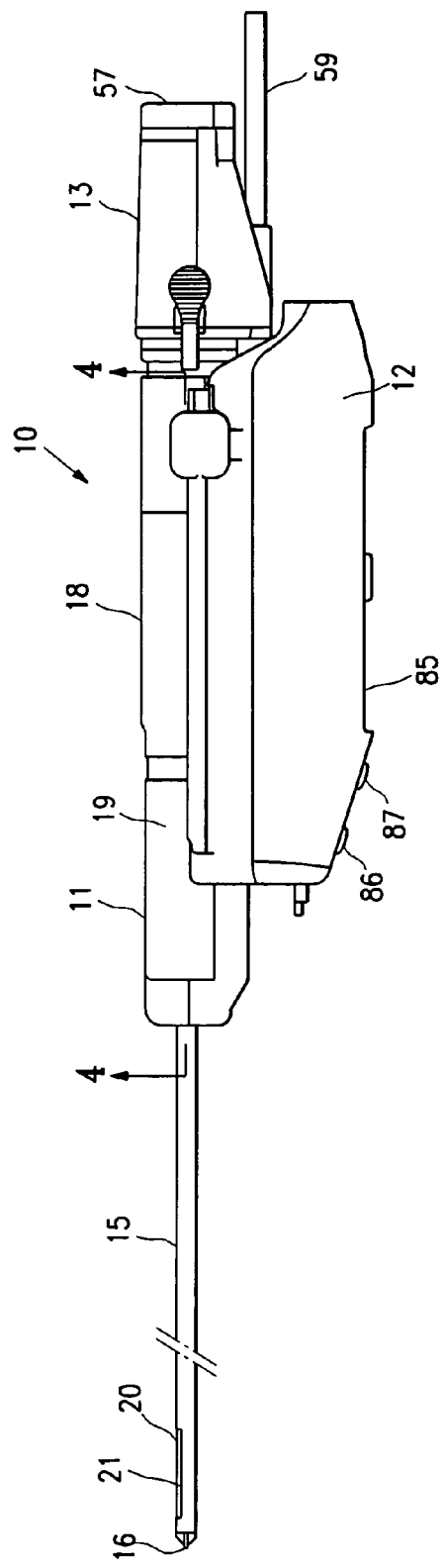
FIG. 3 is a side elevational view of the tissue biopsy device shown in the FIG. 2.

FIGS. 1-3 illustrate a biopsy system 10 embodying features of the invention which includes a disposable probe component 11, a driver component 12 and specimen collector 13.

The probe component 11 generally includes an elongated distal shaft 14 having a tubular section or cannula 15 with a tissue penetrating tip 16 on the distal end thereof and an open, tissue receiving aperture 17. The probe component 11 also includes a probe housing 18 with a housing cover 19 which is configured to interfit with the driver component 12. A tissue cutter 20 is slidably disposed within the probe and has a distal cutting surface 21 which severs tissue which extends through the tissue receiving aperture 17.

Figure 4A:
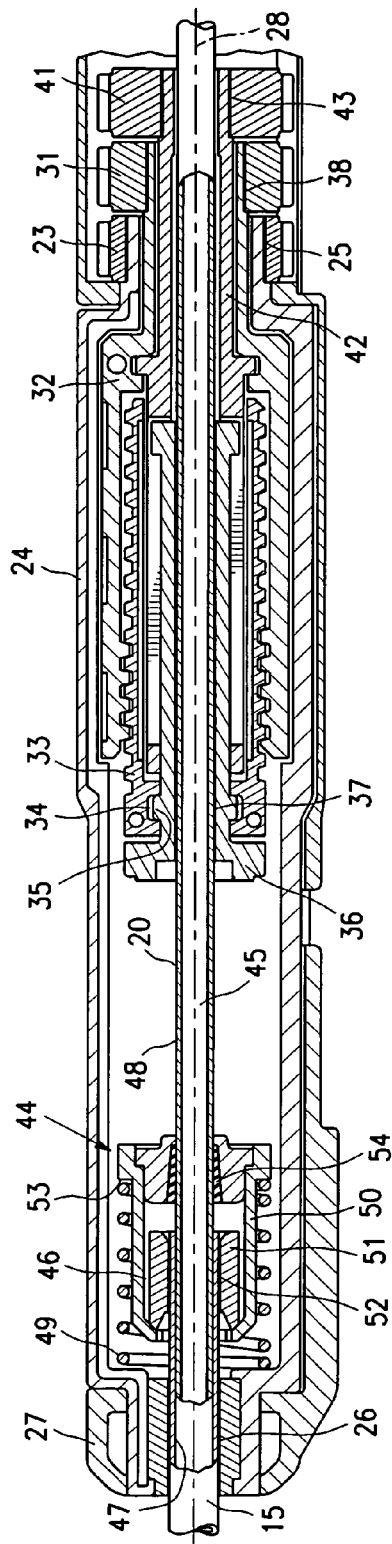
FIG. 4A is a longitudinal cross-section of the probe shown in FIG. 3 taken along the lines 4-4 with the tissue cutting element in a withdrawn position.
Figure 4B:
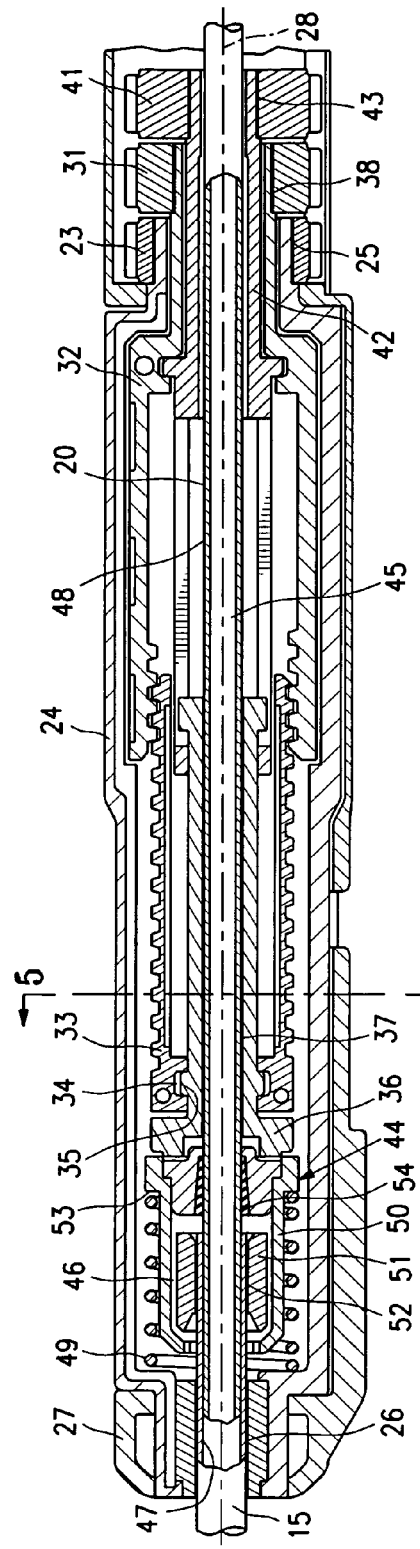
FIG. 4B is a longitudinal cross-section of the probe shown in FIG. 3 taken along the lines 4-4 with the tissue cutting element in a forward or closed position.
Figure 5:
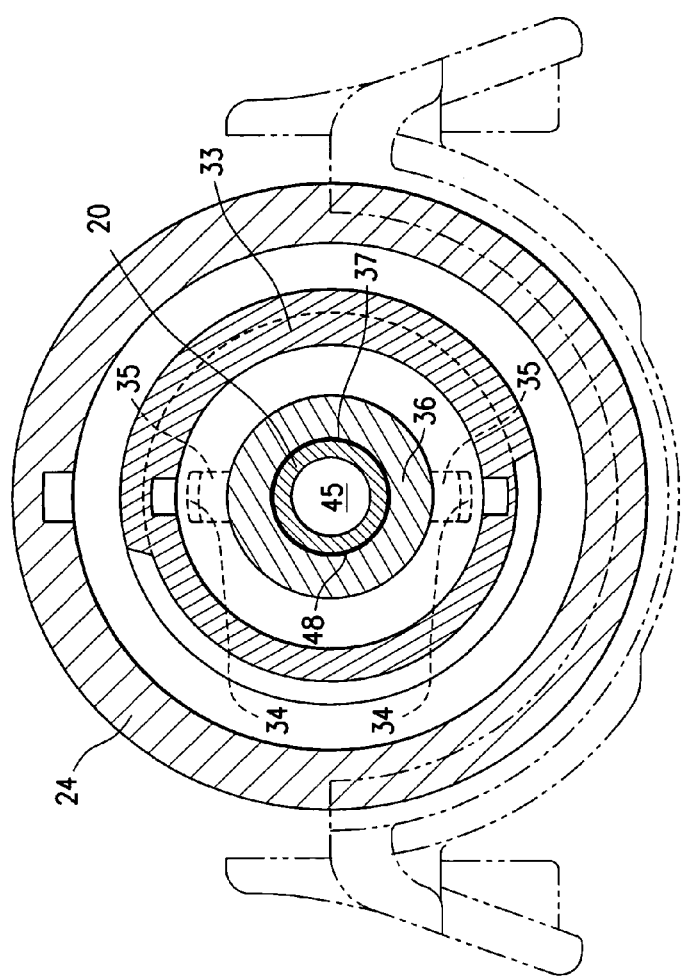
FIG. 5 is a transverse cross-sectional view of the probe shown in FIG. 4B taken along the lines 5-5.
Figure 6:
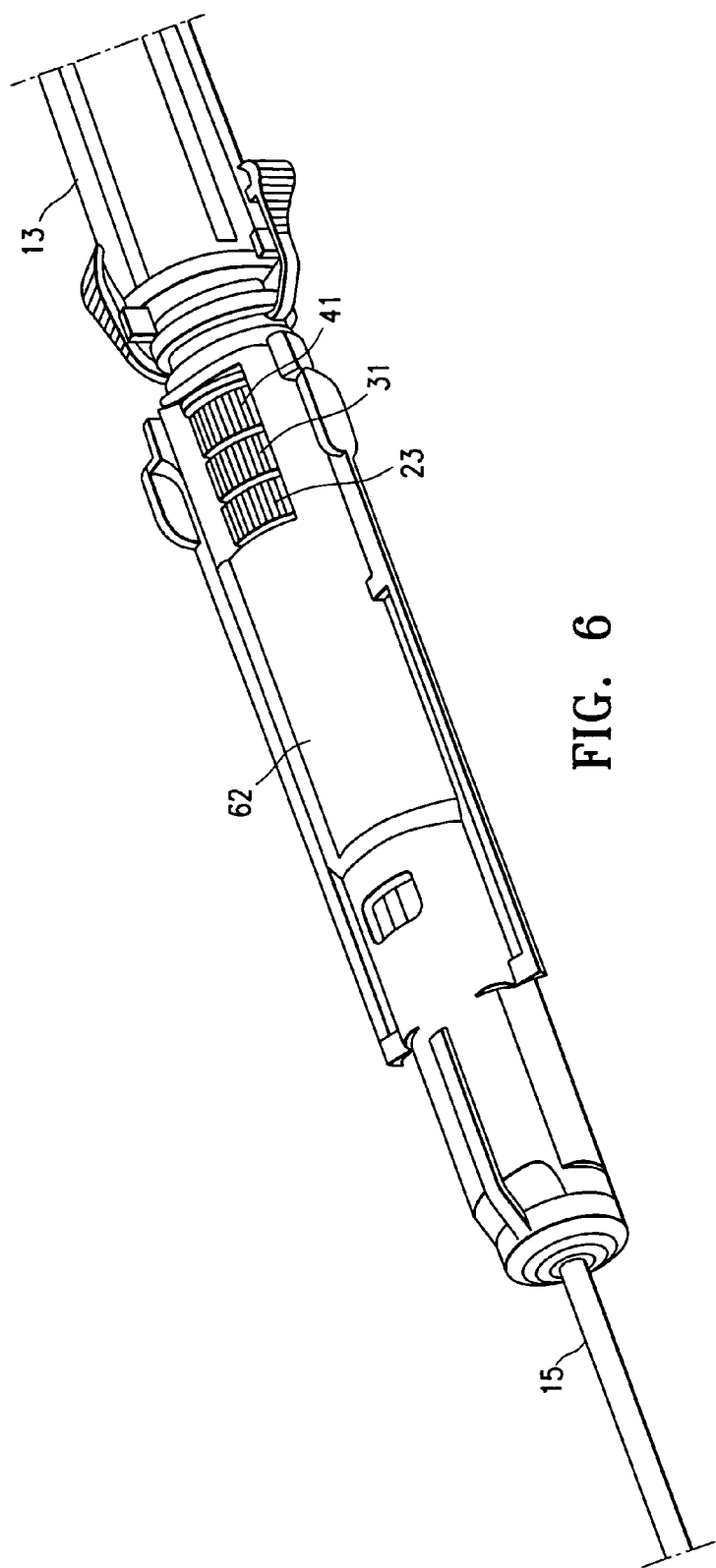
FIG. 6 is a perspective view of the underside of the probe shown in FIG. 1.

Details of the probe component 11 are further shown in FIGS. 4A and 4B. The probe housing 18 has a mechanical system for rotating the housing and the tubular section 15 secured thereto to control the angular position of the tissue receiving aperture 17 and for moving the tissue cutter 20 slidably disposed within the probe component 11.

Figure 8:
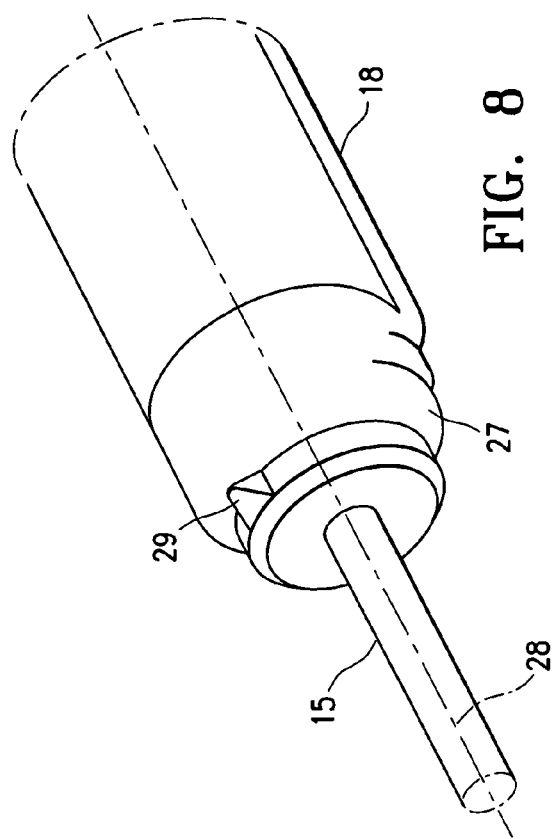
FIG. 8 is an enlarged perspective view of the distal end of the probe housing illustrating a marker element which depicts the orientation of the aperture in the tubular section of the biopsy device.

The mechanical system of the driver component 12 has first driving gear 22 that is configured to engage the probe gear 23 and rotate the probe housing 18 so as to adjust the orientation of aperture 17 in the distal extremity of the tubular section 15. The probe gear 23 is secured to the rotating connector body 24 by adhesive 25. The proximal extremity of the tubular section 15 is secured to the rotating connector body 24 by adhesive 26. An end cap 27 retains the connector body 24 within the probe housing 18. Rotation of the probe gear 23 rotates the connector body 24 and the attached tubular section 15. The rotation is preferably controlled so that the tubular section 15 rotates in discrete steps about the longitudinal axis 28 to adjust the angular orientation of the aperture 17 about the longitudinal axis. Preferably these discrete orientations may be provided in increments of 30° which can be readily indicated by arrow 29 at the distal end of the probe housing 18 as shown in FIG. 8.

The second driving gear 30 is configured to drive the tissue cutter 20 longitudinally. The driving gear 30 engages probe gear 31 which drives cutter traverse nut 32 and cutter screw 33 threadably connected to the cutter traverse nut. The distal end of the cutter screw 33 is provided with a recess 34 which receives the rib 35 of the cutter shuttle 36. The cutter shuttle 36 is secured to the tissue cutter 20 by adhesive 37. The probe gear 31 is secured to the cutter traverse nut 32 by adhesive 38. Rotation of the probe gear 31 adjusts the relative axial position of the cutter screw 33 with respect to the cutter traverse nut 32 which is secured to the cutter shuttle 36. Longitudinal movement of the tissue cutter 20 follows the longitudinal movement of the cutter shuttle 36 resulting from the movement of cutter screw 33. The length of the tissue receiving aperture 17, and as a result the length of the specimen, can be controlled by adjusting the initial longitudinal position of the distal end of the tissue cutter 20 within the aperture, before cutting.

The third driving gear 40 is configured to rotate or oscillate the tissue cutter 20 as the cutter moves along the longitudinal axis 28 to facilitate the cutting action of the cutting surface 21 on the distal end of the cutter. The third driving gear 40 engages probe gear 41 which is secured to cutter oscillation shaft 42 by adhesive 43. The probe gear 41 may be oscillated back and forth about the longitudinal axis 28 or rotated continuously in a single direction about the longitudinal axis, or both depending upon the desired rotational movement of the tissue cutter.

A biased valve assembly 44 is provided in the distal end of the probe housing 18 to ensure sealing when a vacuum is developed within the interior 45 of the tissue cutter 20 while providing an atmospheric vent 46 between the interior surface 47 of the tubular section 15 and the exterior surface 48 of the tissue cutter 20. The valve assembly 44 includes a spring 49, valve body 50 and a valve collar 51 which is secured to the proximal end of the tubular section 15 by adhesive 52. The proximal end of the valve spring 49 rests against the shoulder 53 provided in the exterior of the valve body 50. A biased cutter shaft seal 54 slidably engages the exterior 48 of the tissue cutter 20.

The tissue specimen collector 13 is secured to the proximal end of the housing of probe component 11 and has an interior 55 in fluid communication with the inner lumen 45 extending within the tissue cutter 20 and has a removable proximal wall 57 of specimen receiving cartridge 58 which gives access to the interior 55 and any tissue specimens which may have been drawn therein. A vacuum is generated within the interior 55 to draw tissue specimens through the inner lumen 45 into the interior 55. Tubular member 59 has a distal end which is in fluid communication with the interior 55 of the tissue specimen collector 13 and has a proximal end (not shown) which is configured to be connected to a vacuum source. Application of a vacuum within the tubular member 59 aids in pulling tissue into the interior 17 of the tubular section 15 and transfer of the severed tissue specimen through the inner lumen 45 of the tissue cutter 20 to the specimen cartridge 58.

The driver 12 has a housing 60 with an upper concave surface 61 which is configured to receive the lower surface 62 of the probe housing 18. Three partially exposed driving gears 22, 30 and 40 are provided on the proximal end of the driver 12 which are configured to engage the probe gears 23, 31 and 41 respectively. The drive 12 is provided with three separately operating drive motors (not shown) which drive the drive gears 22, 30 and 40. The separate drive motors (not shown) are connected to and the operation thereof controlled by a control module, such as described in copending application Ser. No. 10/847,699, filed on May 17, 2004. The control module controls the motors which move the individual drive gears 22, 30 and 40. The gear 22 engages gear 23 in the probe 11 to control the rotation of the probe housing 18 and the location and orientation of the tissue receiving aperture 17. The drive gear 30 engages probe gear 31 to control the longitudinal position and motion of the tissue cutter 20 along the longitudinal axis 28. Drive gear 40 engages probe gear 41 to control the oscillation or rotation of the tissue cutter 20 about the longitudinal axis 28.

Figure 7:
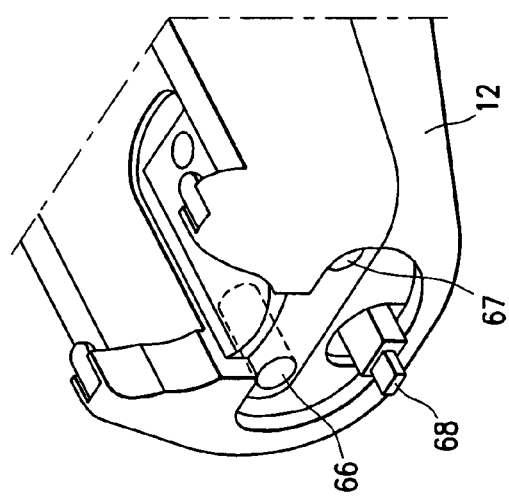
FIG. 7 is an enlarged perspective view of the distal end of the driver unit shown in FIG. 1.

As shown in FIG. 7, the front face of the driver component 12 is provided with light sources 66 and 67 and a manually activatable switch 68 to activate the light sources and enable the physician and other operating personnel to better view the operating site on the patient. Other manual switches, e.g. a foot activated switch, may be employed. Alternatively, the light sources may be automatically activated when the probe component 11 is installed on the driver 12 or other events such as when electrical power is turned on. The driver component 12 may have a battery pack for the light sources 66 and 67.

The penetrating distal tip 16 may have a variety of tip shapes. A particularly suitable distal tip shape is described in co-pending provisional application Ser. No. 60/532,277, filed on Dec. 23, 2003. Alternatively, the distal tip may be provided with an arcuate RF electrode such as disclosed in U.S. Pat. No. 6,261,241, and U.S. Pat. No. 6,471,700, both assigned to the present assignee.

The separate driver component 12 allows the entire probe unit to be disposable. The drive gears of the drive component 12 control the motion of the tissue cutting member 20 for cutting and the motion of the tubular section 15 to orient the aperture 17. Other means (not shown) may provide mechanical and electrical power, vacuum, and control to the probe device. Examples of replaceable snap-in type probe units are disclosed in Burbank et al., U.S. patent application Ser. No. 10/179,933, "Apparatus and Methods for Accessing a Body Site" hereby incorporated by reference in its entirety. Drive units such as that described in WO 02/069808 (which corresponds to co-pending U.S. application Ser. No. 09/707,022, filed Nov. 6, 2000 and U.S. application Ser. No. 09/864,021, filed May 23, 2001), which are assigned to the present assignee, may be readily modified by those skilled in the art to accommodate the movement of the cutting member 20.

The distal end of the probe component 11 is advanced within the patient with the tissue cutter 20 in a forward or closed position (FIG. 4B), until the aperture 17 of the tubular section 15 is located in a desired location for taking a tissue specimen. The tissue cutter 20 is then withdrawn proximally to an open position to open the aperture 17. The withdrawal of the tissue cutter can be used to control the length of the aperture which is opened in order to control the length of the specimen which is severed. A vacuum is applied to the interior 45 of the tissue cutter 20 to draw tissue at the site into the inner lumen of the tubular section 15 through the aperture 17. The tissue cutter 20 is then driven distally by rotation of probe gear 30 and rotated or oscillated by drive gear 40 engaging probe gear 41 to sever the aspirated tissue from the supporting tissue at the target site with the tissue cutting surface 21. The vacuum within the interior of the tissue cutter 20 causes the tissue specimen to be drawn through the inner lumen 45 of the tissue cutter 20 and into the cartridge 58 of specimen collector 13 shown in FIG. 2. Positive pressure or even ambient conditions distal to the tissue specimen can facilitate tissue passing through the interior 45 of tissue cutter 20. If another tissue specimen is desired, the tubular section 15 may be rotated by the drive gear 22 engaging the probe gear 23 in one or more steps to repeat obtaining another tissue specimen in the same manner without otherwise moving the probe component 11. Typically, a first tissue specimen is obtained with the aperture 17 of the probe 11 in the 12 o-clock position, the second at the 3 o-clock position, the third at the 9 o-clock position and the fourth at the 6 o-clock position. The location of the second and third specimens may be reversed. The position of the aperture 17 may be indicated by a marker arrow 29 at the end cap 27 so that the physician or other operating personnel can readily determine what the orientation of the aperture 17 within the patient.

Figure 9:
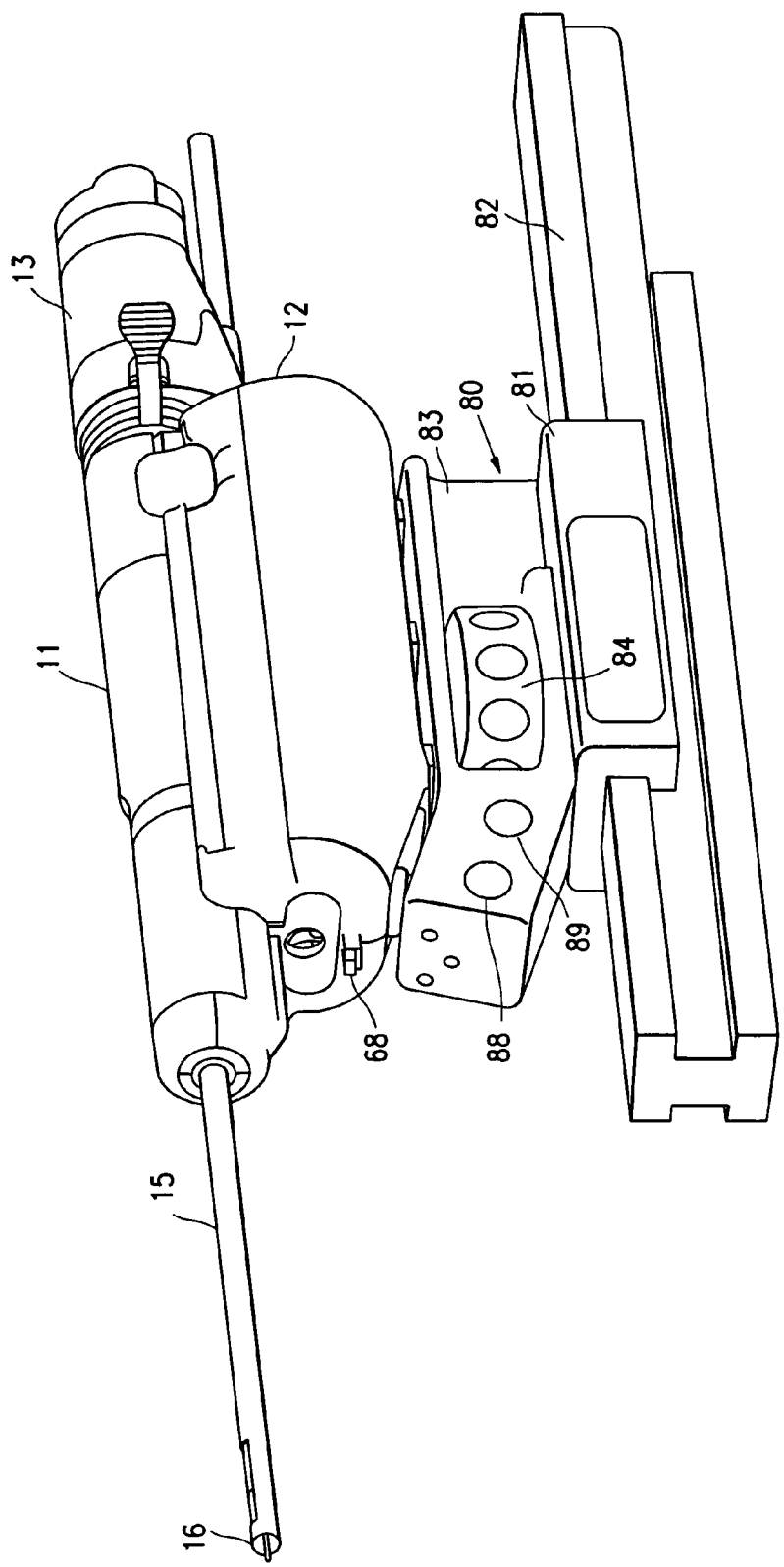
FIG. 9 is a perspective view of the tissue biopsy system shown in FIG. 1 assembled and mounted on a stereotactic frame.
Figure 10:
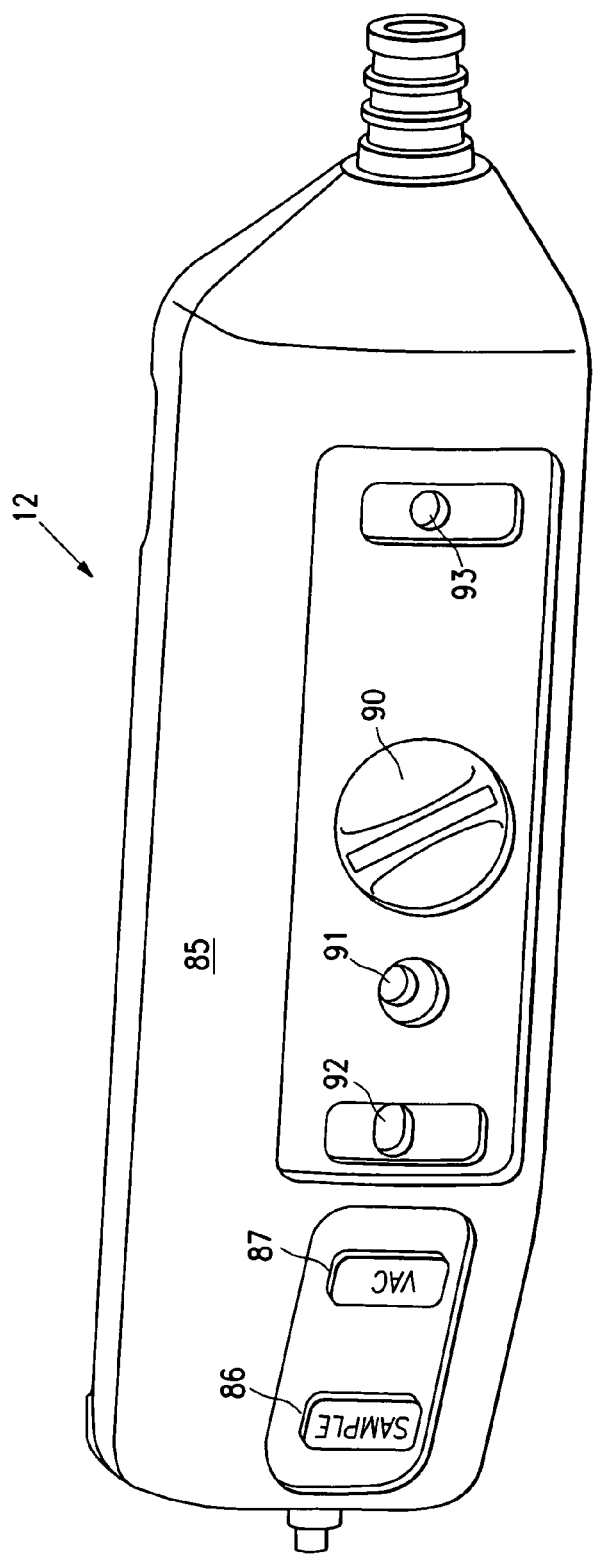
FIG. 10 is a perspective view of the underside of the driver shown in FIG. 1.

The biopsy system 10 may be hand held for some biopsy procedures or the system may be mounted on a stereotactic mounting stage 80 as shown in FIG. 9. A shoe 81 is slidably mounted to a rail 82 of a Fisher stage. The mounting member 83 is secured to the shoe 81 by a threaded post (not shown) secured to thumbwheel 84. As shown in FIG. 10, the bottom surface 85 of the driver component 12 is configured to conform at least in part to the upper surface of the mounting member 83. The sampling and vacuum switches 86 and 87 respectively on the driver component 12 are actuated by the optional sampling and vacuum actuating elements 88 and 89 on the mounting member 83. Alternatively, sampling and vacuum may be actuated with a foot pedal. As shown in FIG. 10, the driver component has an operator dial 90 which when turned opens a threaded hole 91 for receiving a threaded post (not shown) secured to the thumbwheel 84 and the locating pin holes 92 and 93 which receive the complementary posts (not shown) in the mounting member 83.

As mentioned above, positive pressure or even ambient conditions will aid in passing the severed tissue specimen through the inner lumen 45 of tissue cutter 20 into the cartridge 58 of specimen collector 13. As shown in FIGS. 4A and 4B venting valve can provide ambient pressure behind the tissue specimen in the cutter interior 45 from the interior of the tubular section 15. The valve body 50 is opened for atmospheric venting when the tissue cutter 20 is in the forward position upon the completion of severing the specimen from the tissue site. However, when the tissue cutter 20 is pulled back proximally the valve spring 49 urges the valve body 50 back to a closed position. While the tissue cutter 20 is shown with a tissue cutting surface 21 which is perpendicular to the longitudinal axis 28, the tissue cutting surface may be at an angle or even parallel to the longitudinal axis as described in co-pending application Ser. No. 10/642,406, filed Aug. 15, 2003.

The distal cutting edge 21 of the tissue cutter 20 may initially be located proximal to the aperture 17 to provide a full aperture for receiving tissue or it can be initially located within the aperture 17 in order to control the length of the specimen. The cutting action of tissue cutter 20 preferably continues until the beveled cutting surface 21 has completely traversed the aperture 17 to ensure that the tissue drawn through the aperture is completely severed from supporting tissue at the biopsy site. A vacuum may be applied to aspirate the severed tissue specimen through the inner lumen of the tissue cutter 20 to the cartridge in the specimen collector at the proximal end of the biopsy device. Positive pressure or access to ambient conditions may be provided in the distal end of the tubular section to aid in the specimen transfer.

After the removable wall 57 of the specimen receiving cartridge 58 is removed and the specimens therein removed, it is frequently desirable to deliver one or more markers to the target site from which the specimens have been removed. Such marker delivery devices are shown in co-pending application Ser. No. 10/753,694, filed on Jan. 7, 2004 and co-pending application Ser. No. 10/444,770, filed May 23, 2003. However, the distal ends of these marker delivery devices are very small and they can be difficult to insert into the proximal end of the tissue cutter 20 which is just slightly larger to accommodate the marker delivery shaft.

Figure 11:
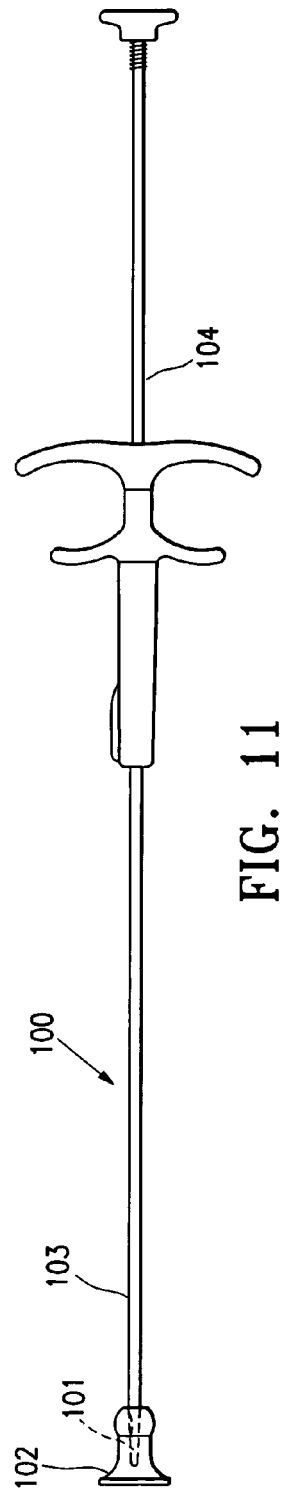
FIG. 11 is an elevational view of a marker delivery device with a flared guide on the distal end of the shaft which facilitates guiding the distal tip of a marker delivery device into the interior of the proximal end of the tissue cutter.
Figure 12:
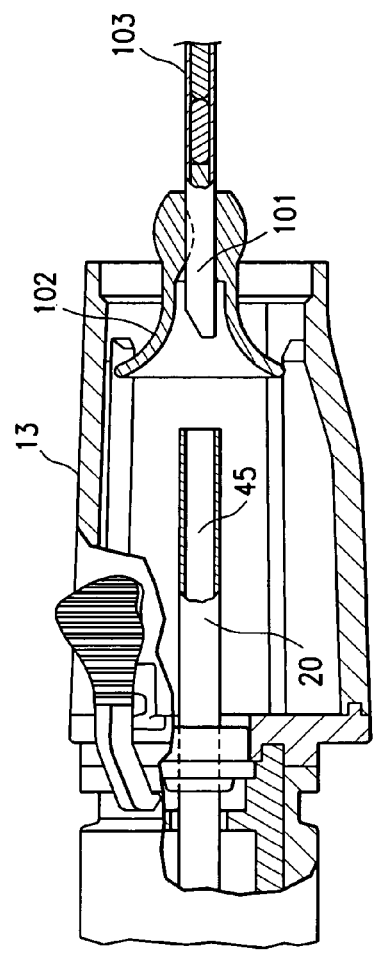
FIG. 12 is a longitudinal cross-sectional view of the distal end of the marker delivery device and flared guide disposed within the tissue collection component shown in FIG. 1.
Figure 13:
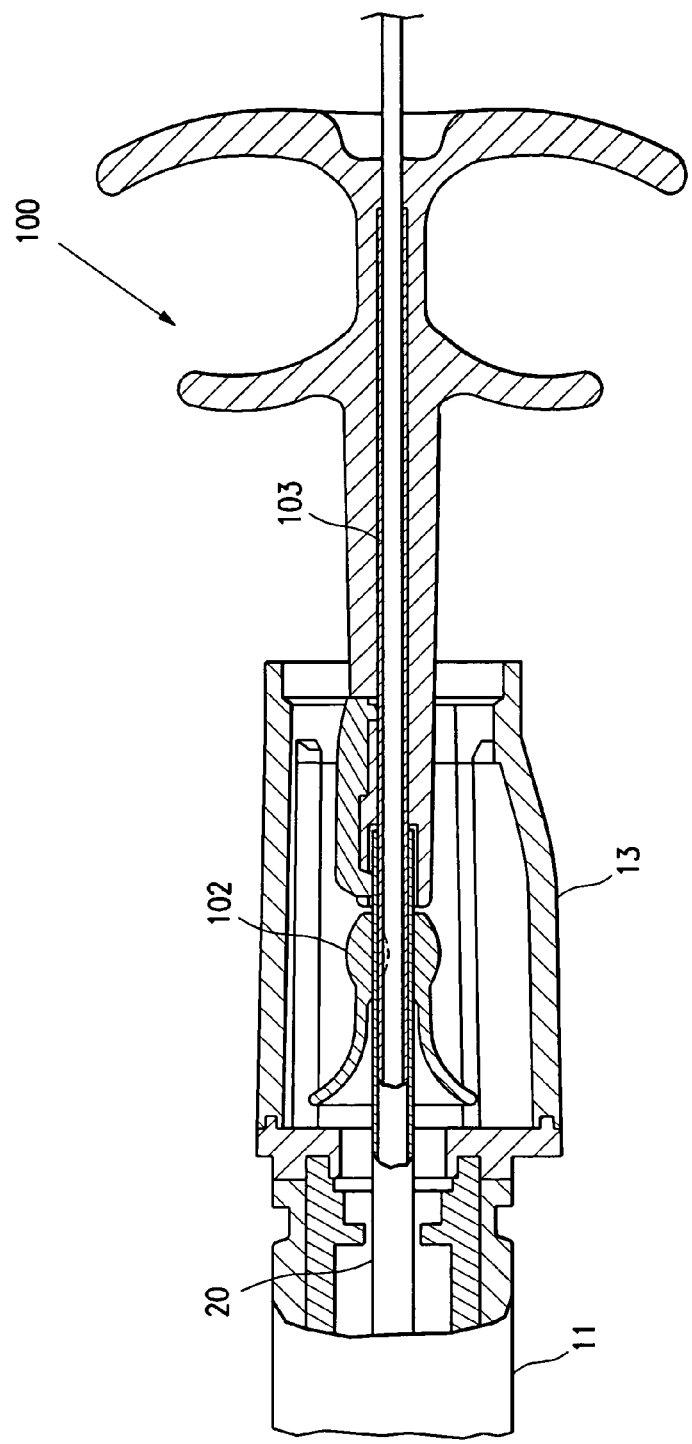
FIG. 13 is a longitudinal cross sectional view of the proximal end of the marker delivery device with the flared guide at the proximal end of the shaft and with the shaft deployed within the inner lumen of the tissue cutter.

FIGS. 11-13 illustrate a marker delivery device 100 which is particularly suitable to facilitate the introduction of the distal end of the shaft 101 into the inner lumen 45 of the tissue cutter 20 and the advancement therein. As indicated into the inner lumen 45 of the tissue cutter 20 to eject one or more markers through the aperture 17 in the tubular section 15 before the biopsy device 10 is removed from the patient. As shown in FIG. 12, to aid in the insertion of the small diameter distal tip 101 of a marker delivery device 100 into the slightly larger inner lumen 45 of the tubular cutter 20 at its proximal end, the distal tip is preferably provided with an outwardly flared guide 102 which is slidably mounted on the shaft 103 of the marker delivery device 100. The proximal end of the tubular cutter 20, the flared guide 102 and/or the distal tip 101 may be provided with mating guide elements which orient the marker delivery device so that one or more markers are discharged through the aperture 17 when the pusher element slidably disposed within the delivery device is urged distally to press at least one marker body out the discharge opening in the distal portion of the elongated shaft of the marker delivery device. The delivery of markers to the target site after specimen removal, while the distal end of the biopsy device is still at the biopsy site, ensures that the markers are properly position at the biopsy site. While the slidably mounted, flared proximal guide 102 is described with respect to being disposed on the shaft 103 of marker delivery device 100, the flared guide 102 has wide application within a variety of biopsy and other devices where one small diameter tubular member is to be inserted into a slightly larger, but still small diameter second tubular member.

The elongated probe component 11 of the biopsy system 10 has a length of about 3 to about 20 cm, preferably, about 5 to about 13 cm, and more specifically, about 8 to about 9 cm for breast biopsy use. To assist in properly locating the probe 11 during advancement thereof into a patient's body, the distal extremity of the tubular section may be provided with a marker at a desirable location that provide enhanced visualization by eye, by ultrasound, by X-ray, MRI or other imaging or visualization means. Manual palpation may also be employed. An echogenic polymer coating that increases contrast resolution in ultrasound imaging devices (such as ECHOCOAT™ by STS Biopolymers, of Henrietta, N.Y.) is suitable for ultrasonic visualization. Radiopaque markers may be made with, for example, stainless steel, platinum, gold, iridium, tantalum, tungsten, silver, rhodium, nickel, bismuth, other radiopaque metals, alloys and oxides of these metals. In addition, the surfaces of the device in contact with tissue or other components of the device may be provided with a suitable lubricious coating such as a hydrophilic material or a fluoropolymer.

The tubular section and the tissue cutter are preferably formed of a surgical grade stainless steel. However, other high strength materials such as MP35N, other cobalt-chromium alloys, NiTi alloys, ceramics, glasses, and high strength polymeric materials or combinations thereof may be suitable.

A patient's skin usually must be breached in order to gain access to a body site where a tissue specimen is to be obtained. A scalpel or other surgical instrument may be used to make an initial incision in the skin. After the specimens have been taken, the biopsy device may be removed from the patient. The entire device may be removed; however, in some embodiments, the cartridge 58 may be removed from the system 10 and a delivery cannula may be inserted through the inner lumen of the cutter 20 to deliver markers to the biopsy site through the aperture 17. In addition, it will be readily appreciated that other types of instruments may be inserted into the tissue site through the tissue cutter in addition to or in place of the instruments described above. Moreover, therapeutic or diagnostic agents may be delivered through the tissue cutter 20 or the tubular section 15.

FIG. 14 illustrates a screen 104 providing certain useful information with respect to an operation of the tissue biopsy system, according to one embodiment of the present invention. The screen 104 can be provided by any type of displays, such as liquid crystal displays (LCD's), cathode ray tube (CRT) monitors and plasma displays. The displays can be used in association with a control module that controls electrosurgical instruments, such as the biopsy system in FIG. 1. For example, the screen 104 can be provided a CM3000 Display used in association with a CM3000 Control Module by SenoRx, Inc.

The screen 104 provides a first textual message 106 showing various states of operation for the biopsy system. For example, the states of operation may include an initialization, calibration, closed, opening, sampling, indexing, indexing error, tool failure, vacuum failure, and tool exit state. These states represent various stages of preparing the biopsy system, taking a tissue specimen from a patient with the biopsy system, and errors occurred during the preparing and taking processes. A second textual message 108 on the screen 104 details the status of the particular state shown by the first textual message 106. For example, on the screen 104, the second textual message 108 tells a user to wait for the completion of an opening state, in which the biopsy system performs an open stroke. At the bottom of the screen 104 are indicators 110 for indicating certain events or conditions. For example, when the indicator 110 that labeled as VAC is on, it tells that a vacuum system is currently running.

The screen 104 further provides a graphical user interface 112 that represents various parts of a target site within a patient from which one or more tissue specimens have been taken or may be taken. The graphical user interface 112 may further represent an angular position of the tissue cutting member 20 shown in FIG. 2. Since the tissue cutting member 20 positions its cutting tip in a target site of a patient's body in a rotational movement, the graphical user interface 112 is designed based on a circular shape. However, it is noteworthy that other shapes capable of representing the angular positions of the tissue cutting member 20 can also be used as the basic shapes for the graphical user interface 112. For example, the graphical user interface 112 may be designed based on a polygonal shape. Various designs for the graphical user interface 112 will be described in the following paragraphs.

FIGS. 15A through 15E illustrate various alternatives of the graphical user interface 112 in FIG. 14, according to one embodiment of the present invention. In this embodiment, the graphical user interface 112 includes a first GUI area representing a first region of a target site from which at least one tissue specimen has been separated from tissue at the target site by the tissue cutting member. The graphical user interface 112 further includes a second GUI area, visually distinguishable from the first GUI area, representing a second region from which the tissue cutting member may separate one or more additional tissue specimens from tissue at the target site. The first and second GUI areas are marked with colors or patterns distinguishable from one another. They visualize the part of the tissue at the target site that has been cut, and the rest of the tissue that may be cut by the biopsy system. This helps a surgeon to better understand the progress of a biopsy operation.

FIG. 15A shows a first alternative of a graphical user interface 114 according to the embodiment. The first GUI area 116 and second GUI area 118 are arranged within a circle. The first GUI area 116 is of a fan shape, and the circle unoccupied by the first GUI area 116 represents the second GUI area 118. In this figure, a smaller angular portion of the tissue at the target site has been cut, while a larger angular portion of the tissue may be cut in a later process of operation.

FIG. 15B shows a second alternative of a graphical user interface 120 according to the embodiment. The shaded part represents the first GUI area 122, and the unshaded part represents the second GUI area 124. The first GUI area 122 includes a first portion 126 of a fan shape at the centric point of the circular shaped graphical user interface 120. The arm of the first portion 126 is smaller than the radius of the graphical user interface 120. The first GUI area 122 further includes a second portion 128 that is shaped as a curvy band in alignment with an arc of the first portion 126. The angle of first portion 126 represents the angular portion of the tissue that has been cut.

FIG. 15C shows a third alternative of a graphical user interface 130 according to the embodiment. The shaded part represents the first GUI area 132, and the unshaded part represents the second GUI area 134. The first GUI area includes a first portion 136 of a circular shape, and a second portion 138 shaped as a curvy band adjacent to a circumferential line of the first portion 136. The two side lines of the second portion 138 define an angle that represents the angular portion of the tissue that has been cut.

FIG. 15D shows a fourth alternative of a graphical user interface 140 according to the embodiment. The shaded part represents the first GUI area 142, and the unshaded part represents the second GUI area 144. The first GUI area 142 includes a first portion 145 of a circular shape, a second portion 146 shaped as a curvy band adjacent to a circumferential line of the first portion, and a third portion 147 shaped as a curvy band in alignment with an outer peripheral line of the second portion 146. The side lines of the second portion 146 or the third portion 147 define an angle that represents the angular portion of the tissue that has been cut.

FIG. 15E shows a fifth alternative of a graphical user interface 150 according to the embodiment. The shaded part represents the first GUI area 152, and the unshaded part represents the second GUI area 154. The first GUI area includes a first portion 155 of a circular shape, a second portion 156 of a ring shape surrounding the first portion 155, and a third portion 157 shaped as a curvy band adjacent to a circumferential line of the second portion 156. The side lines of the third portion 157 define an angle representing the angular portion of the tissue that has been cut.

FIGS. 16A through 16E show another set of alternatives of the graphical user interface 112 in FIG. 14 according to the embodiment of the present invention. FIG. 16A shows a first alternative of a graphical user interface 160. The first GUI area 162 and second GUI area 164 are arranged within a regular polygon. The first GUI area 162 is a divisional portion of the regular polygon with an angle defined at a geometrical center thereof. The reset of the regular polygon unoccupied by the first GUI area 162 represents the second GUI area 164. As discussed above, the first GUI area 162 represents an angular portion of the tissue at the target site that has been cut, while the second GUI area 164 represent the portion of the tissue that may be cut in a later operation process.

FIG. 16B shows a second alternative of a graphical user interface 170 according to the embodiment. The shaded part represents the first GUI area 172, and the unshaded part represents the second GUI area 174. The first GUI area 172 includes a first portion 176 of a polygonal shape with an angle defined at a geometrical center of the regular polygon 179. The first GUI area 174 further includes a second portion 178 shaped as a polygonal band along a peripheral line of the regular polygon 179, in alignment with the first portion 176. The angle of first portion 176 represents the angular portion of the tissue that has been cut.

FIG. 16C shows a third alternative of a graphical user interface 180 according to the embodiment. The shaded part represents the first GUI area 182, and the unshaded part represents the second GUI area 184. The first GUI area 182 includes a first portion 186 of a polygonal shape having a geometrical center the same as that of the regular polygon 189. The first GUI area 180 further includes a second portion 188 shaped as a polygonal band along a peripheral line of the regular polygon 189, adjacent to an outer peripheral line of the first portion 186. The two side lines of the second portion 188 define an angle representing the angular portion of the tissue that has been cut.

FIG. 16D shows a fourth alternative of a graphical user interface 190 according to the embodiment. The shaded part represents the first GUI area 192, and the unshaded part represents the second GUI area 194. The first GUI area 192 includes a first portion 195, second portion 196 and third portion 197. The first portion 195 is of a polygonal shape having a geometrical center the same as that of the regular polygon 198. The second portion 196 is shaped as a polygonal band adjacent to an outer peripheral line of the first portion 195. The third portion 197 is shaped as a polygonal band along a peripheral line of the regular polygon 198, in alignment with an outer peripheral line of the second portion 196. The two side lines of the second portion 196 or the third portion 197 define an angle representing the angular portion of the tissue that has been cut.

FIG. 16E shows a fifth alternative of a graphical user interface 200 according to the embodiment. The shaded part represents the first GUI area 202, and the unshaded part represents the second GUI area 204. The first GUI area 202 includes a first portion 205, second portion 206 and third portion 207. The first portion 205 is of a polygonal shape having a geometrical center the same as that of the regular polygon 208. The second portion 206 is shaped as a polygonal ring surrounding the first portion 205. The third portion 207 is shaped as a polygonal band along a peripheral line of the regular polygon 208, adjacent to an outer peripheral line of the second portion 206. The two side lines of the third portion 207 define an angle representing the angular portion of the tissue that has been cut.

In the above embodiment, while none of the various graphical user interfaces shows a current angular position of the tissue cutting member, it can be known by an external indicator 29 shown in FIG. 8.

FIGS. 17A through 17E illustrate various alternatives of the graphical user interface 112 in FIG. 14, according to another embodiment of the present invention. In this embodiment, the graphical user interface 112 includes a first, second and third GUI areas. The first GUI area represents a first region of a target site from which at least one tissue specimen has been separated from tissue at the target site by the tissue cutting member. The second GUI area, visually distinguishable from the first GUI area, represents a second region from which the tissue cutting member may separate one or more additional tissue specimens from tissue at the target site. The third GUI area, visually distinguishable from the first and second GUI areas, represents a third region in which the tissue cutting member is deployed to separate a tissue specimen from tissue at the target site. The first, second and third GUI areas are marked with colors or patterns distinguishable from each other. They visualize the part of the tissue at the target site that has been cut, the rest of the tissue that may be cut, and the angular position where the cutting member is at. This helps a surgeon to better understand the progress of a biopsy operation.

FIG. 17A shows a first alternative of a graphical user interface 210 according to the embodiment. The first GUI area 202, second GUI area 204 and third GUI area 206 are arranged within a circle 208. The first GUI area 202 and the third GUI area 206 are of a fan shape. The circle unoccupied by the first GUI area 202 and third GUI area 206 represent the second GUI area 118.

FIG. 17B shows a second alternative of a graphical user interface 220 according to the embodiment. The graphical user interfere face 220 differs from that in FIG. 15B in having a third GUI area 222, which includes a first portion 223 and second portion 224. The first portion 223 of the third GUI area 222 is of a fan shape concentric with a first portion 225 of the first GUI area 226. The second portion 224 of the third GUI area 222 is shaped as a curvy band in alignment with an arc of the first portion 223 of the third GUI area 222.

FIG. 17C shows a third alternative of a graphical user interface 230 according to the embodiment. The graphical user interfere face 230 differs from that in FIG. 15C in having a third GUI area 232, which is shaped as a curvy band adjacent to the circumferential line of a first portion 234 of the first GUI area 236.

FIG. 17D shows a fourth alternative of a graphical user interface 240 according to the embodiment. The graphical user interfere face 240 differs from that in FIG. 15D in having a third GUI area 242, which includes a first portion 243 and second portion 244. The first portion 243 of the third GUI area 242 is shaped as a curvy band adjacent to the circumferential line of a first portion 245 of the first GUI area 246. The second portion 244 of the third GUI area 242 is also shaped as a curvy band in alignment with an outer peripheral line of the second portion 242.

FIG. 17E shows a fifth alternative of a graphical user interface 250 according to the embodiment. The graphical user interfere face 250 differs from that in FIG. 15E in having a third GUI area 252, which is shaped as a curvy band adjacent to the circumferential line of a ring 254 of the first GUI area 256.

FIGS. 18A through 18E show another set of alternatives of the graphical user interface 112 in FIG. 14 according to the embodiment of the present invention. FIG. 18A shows a first alternative of a graphical user interface 260. The graphical user interface 260 differs from that in FIG. 16A in having a third GUI area 262, which is a divisional portion of the regular polygon 264 with an angle defined at a geometrical center the regular polygon 265.

FIG. 18B shows a second alternative of a graphical user interface 270. The graphical user interface 270 differs from that in FIG. 16B in having a third GUI area 272, which includes a first portion 273 and a second portion 274. The first portion 273 of the third GUI area 272 is of a polygonal shape with an angle defined at the geometrical center of the regular polygon 275. The second portion 274 of the third GUI area 272 is shaped as a polygonal band along the peripheral line of the regular polygon 275, in alignment with outer peripheral line of the first portion 273.

FIG. 18C shows a third alternative of a graphical user interface 280. The graphical user interface 280 differs from that in FIG. 16C in having a third GUI area 282, which is shaped as a polygonal band along a peripheral line of the regular polygon 284.

FIG. 18D shows a fourth alternative of a graphical user interface 290. The graphical user interface 290 differs from that in FIG. 16D in having a third GUI area 292, which includes a first portion 293 and a second portion 294. The first portion 293 of the third GUI area 292 is shaped as a polygonal band adjacent to an outer peripheral line of an inner polygon 296. The second portion 294 of the third GUI area 292 is shaped as a polygonal band along the peripheral line of the regular polygon 295, adjacent to an outer peripheral line of the first portion 293.

FIG. 18E shows a fifth alternative of a graphical user interface 300. The graphical user interface 300 differs from that in FIG. 16E in having a third GUI area 302, which is shaped as a polygonal band along a peripheral line of the regular polygon 304, adjacent to a polygonal ring 306.

As discussed above, the first, second and third GUI areas visualize the part of the tissue at the target site that has been cut, the rest of the tissue that may be cut, and the current angular position where the tissue cutting member is at. This helps a surgeon to better understand the progress of a biopsy operation.

While particular forms of the invention have been illustrated and described herein, it will be apparent that various modifications and improvements can be made to the invention. For example, while the various embodiments of the invention have been described herein in terms of a biopsy device, it should be apparent that the devices and methods of utilizing the device may be employed to remove tissue for purposes other than for biopsy, i.e. for treatment or other diagnoses. Other modifications include, for example, a tissue cutter slidably mounted around the tubular section of the probe component rather than within the tubular section. Moreover, individual features of embodiments of the invention may be shown in some drawings and not in others, but those skilled in the art will recognize that individual features of one embodiment of the invention can be combined with any or all the features of another embodiment. Accordingly, it is not intended that the invention be limited to the specific embodiments illustrated. It is therefore intended that this invention to be defined by the scope of the appended claims as broadly as the prior art will permit.

Terms such a "element", "member", "device", "section", "portion", "component", "means", "step" and words of similar import, when used herein, shall not be construed as invoking the provisions of 35 U.S.C. §112(6) unless the following claims expressly use the term "means" followed by a particular function without specific structure or the term "step" followed by a particular function without specific action. All patents and patent applications referred to above are hereby incorporated by reference in their entirety.

What is claimed is:

1. A tissue biopsy system, comprising:
a probe component that includes an elongated distal shaft having a cannula with a tissue penetrating tip and a tissue receiving aperture;
a tissue cutting member movable relative to the probe component, and configured to sever tissue which extends through the tissue receiving aperture;
a driver component configured to rotate the probe component so as to adjust a rotational orientation of the tissue receiving aperture to each of a plurality of rotational positions;
a graphical user interface (GUI) configured to generate a positional representation of each rotational position of the tissue receiving aperture to display a graphical representation of a cutting progression during a biopsy procedure,
the GUI configured to generate during the biopsy procedure a first angular GUI area graphical representation of a first region of a target site corresponding to at least one rotational position of the tissue receiving aperture from which the tissue cutting member has severed tissue which extends through the tissue receiving aperture, the first angular GUI area having a first artificial visual identifying characteristic; and
the GUI configured to generate during the biopsy procedure a second angular GUI area graphical representation of a second region of the target site corresponding to a remainder of the plurality of rotational positions of the tissue receiving aperture from which the tissue cutting member has not separated any tissue specimen, the second angular GUI area having a second artificial visual identifying characteristic to make the second angular GUI area visually distinguishable from the first angular GUI area.

2. The tissue biopsy system of claim 1 wherein the first angular GUI area is marked with the first visual identifying characteristic as a color or pattern to distinguish the first angular GUI area from the second angular GUI area.

3. The tissue biopsy system of claim 1 wherein the first angular GUI area and the second angular GUI area are arranged within a circle.

4. The tissue biopsy system of claim 3 wherein the first angular GUI area is of a fan shape, wherein the first visual identifying characteristic is a color across an extent of the first angular GUI area.

5. The tissue biopsy system of claim 3 wherein the first GUI area comprises a first portion of a fan shape, and a second portion shaped as a curvy band in alignment with the first portion.

6. The tissue biopsy system of claim 3 wherein the first GUI area comprises a first portion of a circular shape, and a second portion shaped as a curvy band adjacent to a circumferential line of the first portion.

7. The tissue biopsy system of claim 3 wherein the first GUI area comprises a first portion of a circular shape, a second portion shaped as a curvy band adjacent to a circumferential line of the first portion, and a third portion shaped as a curvy band in alignment with an outer peripheral line of the second portion.

8. The tissue biopsy system of claim 3 wherein the first GUI area comprises a first portion of a circular shape, a second portion of a ring shape surrounding the first portion, and a third portion shaped as a curvy band adjacent to an outer circumferential line of the second portion.

9. The tissue biopsy system of claim 1 wherein the first and second GUI areas are arranged within a regular polygon.

10. The tissue biopsy system of claim 9 wherein the first GUI area is a divisional portion of the regular polygon with an angle defined at a geometrical center thereof.

11. The tissue biopsy system of claim 9 wherein the first GUI area comprises a first portion of a polygonal shape with an angle defined at a geometrical center of the regular polygon, and a second portion shaped as a polygonal band along a peripheral line of the regular polygon, in alignment with the first portion.

12. The tissue biopsy system of claim 9 wherein the first GUI area comprises a first portion of a polygonal shape having a geometrical center the same as a geometrical center of the regular polygon, and a second portion shaped as a polygonal band along a peripheral line of the regular polygon, adjacent to a peripheral line of the first portion.

13. The tissue biopsy system of claim 9 wherein the first GUI area comprises a first portion of a polygonal shape having a geometrical center the same as a geometrical center of the regular polygon, a second portion shaped as a polygonal band adjacent to a peripheral line of the first portion, and a third portion shaped as a polygonal band along a peripheral line of the regular polygon, in alignment with the second portion.

14. The tissue biopsy system of claim 9 wherein the first GUI area comprises a first portion of a polygonal shape having a geometrical center the same as a geometrical center of the regular polygon, a second portion shaped as a polygonal ring surrounding the first portion, and a third portion shaped as a polygonal band along a peripheral line of the regular polygon, adjacent to an outer peripheral line of the second portion.

15. The tissue biopsy system of claim 1 wherein the biopsy system comprises a biopsy component having an external indicator showing a current angular position of the tissue receiving aperture.

16. The tissue biopsy system of claim 1 further comprising a third GUI area, visually distinguishable from the first and second GUI areas, representing a third region in which the tissue cutting member is deployed to separate a tissue specimen from tissue at the target site.

17. The tissue biopsy system of claim 16 wherein the third GUI area is marked with a color or pattern distinguishable from those marking the first and second GUI areas.

18. The tissue biopsy system of claim 16 wherein the first, second and third GUI areas are arranged within a circle.

19. The tissue biopsy system of claim 18 wherein the third GUI area is of a fan shape.

20. The tissue biopsy system of claim 18 wherein the third GUI area comprises a first portion of a fan shape, and a second portion shaped as a curvy band in alignment with the first portion of the third GUI area.

21. The tissue biopsy system of claim 18 wherein the third GUI area is shaped as a curvy band along a circumferential line of the circle.

22. The tissue biopsy system of claim 18 wherein the third GUI area comprises a first portion shaped as a curvy band along a circumferential line of the circle, and a second portion shaped as a curvy band in alignment with an inner peripheral line of the first portion of the third GUI area.

23. The tissue biopsy system of claim 16 wherein the first, second and third GUI areas are arranged within a regular polygon.

24. The tissue biopsy system of claim 23 wherein the third GUI area is a divisional portion of the regular polygon with an angle defined at a geometrical center thereof.

25. The tissue biopsy system of claim 23 wherein the third GUI area comprises a first portion of a polygonal shape with an angle defined at a geometrical center of the regular polygon, and a second portion shaped as a polygonal band along a peripheral line of the regular polygon, in alignment with the first portion of the third GUI area.

26. The tissue biopsy system of claim 23 wherein the third GUI area is shaped as a polygonal band along a circumferential line of the regular polygon.

27. The tissue biopsy system of claim 23 wherein the third GUI area comprises a first portion shaped as a polygonal band along a circumferential line of the regular polygon, and a second portion shaped as a polygonal band in alignment with an inner peripheral line of the first portion of the third GUI area.

28. The tissue biopsy system of claim 1, wherein the first angular GUI area is increased and the second angular GUI area is decreased when a tissue specimen is separated by the cutting member from the second region of the target site.

29. A tissue biopsy system for use in a biopsy operation, comprising:
   a probe component that includes an elongated distal shaft having a cannula with a tissue penetrating tip and a tissue receiving aperture;
   a tissue cutting member movable relative to the probe component, and configured to sever tissue which extends through the tissue receiving aperture of the probe component to generate a tissue specimen;
   a driver component configured to rotate the probe component so as to adjust the rotational orientation of the tissue receiving aperture to each of a plurality of discrete rotational positions; and
   a graphical user interface (GUI) configured to generate a positional representation of each discrete rotational position of the tissue receiving aperture to display a graphical representation of a cutting progression during a biopsy procedure, and configured to update the positional representation of the plurality of discrete rotational positions during the biopsy operation to indicate each rotational position from which each tissue specimen has been harvested,
   the GUI configured to generate during the biopsy procedure a first GUI area graphical representation of a first region of a target site corresponding to at least one rotational position of the tissue receiving aperture from which the tissue cutting member has severed at least one tissue specimen, the first GUI area graphical representation having a first artificial visual identifying characteristic; and the GUI configured to generate during the biopsy procedure a second GUI area graphical representation of a second region of the target site corresponding to a remainder of the plurality of rotational positions of the tissue receiving aperture from which the tissue cutting member has not separated any tissue specimen, the second GUI area graphical representation having a second artificial visual identifying characteristic to make the second GUI area graphical representation visually distinguishable from the first GUI area graphical representation.

* * * * *